US007847071B2

(12) United States Patent
Bonnerjea et al.

(10) Patent No.: US 7,847,071 B2
(45) Date of Patent: Dec. 7, 2010

(54) ANTIBODY PURIFICATION BY PROTEIN A AND ION EXCHANGE CHROMATOGRAPHY

(75) Inventors: Julian Bonnerjea, High Wycombe (GB); Anna Preneta, Walton-on-Thames (GB)

(73) Assignee: Lonza Biologics PLC., Slough, Berkshire (GB)

( * ) Notice: Subject to any disclaimer, the term of this patent is extended or adjusted under 35 U.S.C. 154(b) by 0 days.

(21) Appl. No.: 11/419,306

(22) Filed: May 19, 2006

(65) Prior Publication Data

US 2006/0194953 A1     Aug. 31, 2006

Related U.S. Application Data

(63) Continuation of application No. 11/210,669, filed on Aug. 25, 2005, now abandoned, which is a continuation-in-part of application No. PCT/EP2004/002041, filed on Mar. 1, 2004.

(60) Provisional application No. 60/604,464, filed on Aug. 26, 2004, provisional application No. 60/464,973, filed on Apr. 24, 2003.

(30) Foreign Application Priority Data

Feb. 28, 2003   (GB) ................................ 0304576.2

(51) Int. Cl.
  *C07K 1/18*   (2006.01)
  *C07K 1/22*   (2006.01)
(52) U.S. Cl. ................. 530/390.5; 424/177.1; 436/548; 530/413; 530/416
(58) Field of Classification Search ............. 424/177.1; 530/390.5, 413, 416; 436/548
  See application file for complete search history.

(56) References Cited

U.S. PATENT DOCUMENTS

| 5,115,101 | A | * | 5/1992 | Bloom et al. ........... 530/388.25 |
| 5,118,796 | A | | 6/1992 | Prior et al. |
| 5,429,746 | A | | 7/1995 | Shadle et al. |
| 5,644,036 | A | * | 7/1997 | Ramage et al. ............. 530/412 |
| 5,650,319 | A | * | 7/1997 | Masuho et al. .............. 435/339 |
| 6,013,763 | A | | 1/2000 | Braisted et al. |
| 6,121,428 | A | | 9/2000 | Blank et al. |
| 6,177,548 | B1 | | 1/2001 | Wan et al. |
| 6,307,028 | B1 | | 10/2001 | Lebing et al. |
| 7,122,641 | B2 | * | 10/2006 | Vedantham et al. .......... 530/413 |
| 2005/0107594 | A1 | * | 5/2005 | Sun et al. .................. 530/387.1 |
| 2006/0257972 | A1 | * | 11/2006 | Ishihara ..................... 435/69.1 |
| 2008/0312425 | A1 | | 12/2008 | Bonnerjea |

FOREIGN PATENT DOCUMENTS

| CA | 1 201 063 | 2/1986 |
| EP | 282 308 | 9/1988 |
| EP | 0284368 | * 9/1988 |
| EP | 0 289 129 | 11/1988 |
| EP | 0 345 549 | 12/1989 |
| EP | 0 481 089 | 4/1992 |
| EP | 0 282 308 | 9/1998 |
| EP | 1 601 697 B1 | 5/2007 |
| JP | 07-155194 A | * 6/1995 |
| JP | 7155194 | 6/1995 |
| WO | WO 92/18629 | 10/1992 |
| WO | WO 97/17361 | 5/1997 |
| WO | WO 98/56808 | 12/1998 |
| WO | WO 99/62936 | 12/1999 |
| WO | WO 00/44772 | 8/2000 |
| WO | WO 01/57090 | 8/2001 |

OTHER PUBLICATIONS

AIPN Japan Patent Office, machine translation of JP 7-155194 A, Oct. 28, 2007, pp. 1 and 5-16.*
Glennie et al, Drug Discovery Today, vol. 8, No. 11, pp. 503-510, 2003.*
Jiskoot et al, Developments in Biological Standarization 1990, vol. 71, pp. 73-78.
Blank et al, Bioseparatlon, 2001, vol. 10, No. 1-3, pp. 65-71.
Gagnon P., Purification Tools for Monoclonal Antibodies; Chapter 9 with the title "Protein A Affinity Chromatography", 1996.
Kawabata et al, "Optimization and Validation of an ELISA to Measure Specific Guinea Pig IgG1 Antibody as an Alternative to the in Vivo Passive Cutaneous Anaphylaxis Assay", Fundamental and Applied Toxicology, vol. 24, 1995, 238-246, 1995.
Gagnon et al, A systematic approach to the purification of monoclonal antibodies, Validated iosyst., Menlo Park, CA, USA. LC-GC, 11(1), 26-8, 30,32,34. CODEN: LCGCE7 ISSN: 0888-9090. Journal written in English. CAN 118:145356 AN 1993:145356 CAPLUS; 1993.
Lindmark R. et al., "Quantitation of Specific IgG Antibodies in Rabbits by a Solid-phase Radioimmunoassay with $^{125}$I-Portein A from *Staphylococcus aureus*", Scand. J. Immunol. 14; pp. 409-420, 1981.
Hahn R. et al., "Comparison of protein A affinity sorbents", Journal of Chromatography; B 790, 35-51, 2003.
Surolia et al., "Protein A: nature's universal anti-antibody", TIBS Feb. 1982, 74-76; Feb. 1982.
Hanna L.S. et al., "Removing Specific Cell Culture Contaminants in a MAb Purification Process", Biopharm,; 33-37; Oct. 1991.
Fahrner R. L. et al., "Industrial Purification of Pharmaceutical Antibodies: Development, Operation, and Validation of Chromatography Processes", Biotechnology and Genetic Engineering Reviews vol. 18; 301-327, Jul. 2001.

(Continued)

*Primary Examiner*—David A Saunders
(74) *Attorney, Agent, or Firm*—Nixon & Vanderhye P.C.

(57) ABSTRACT

A novel method for selectively removing leaked protein A from antibody purified by means of protein A affinity chromatography is disclosed.

24 Claims, 5 Drawing Sheets

OTHER PUBLICATIONS

Mitra G. et al., "Protein Purification in Preparative Scale of Mammalian Cell Culture-Derived Products", Ann. N.Y. Acad. Sci.; 782, 422-31; 1996.

Crapper and Schrader, "Antibody stimulation of hemopoletic progenitor cells", Blood, 65:869-876; 1985.

Scopes, Robert K., Protein Purification—Principles and Practice, 2. Ed. 121/122; 1988.

Janson/Rydén, "Principles, High-Resolution Methods, and Applications", (Hrsg.), Protein Purification, 2. Ed. 175-177; 1998.

Friesen, A.D. et al., "Column Ion exchange Chromatographic Production of Human Immune Serum Globulin for Intravenous Use", Vox. Sang 48:201-212; 1985.

O'Leary et al, "Determining the Useful Lifetime of Chromatography Resins"; BioPharma Sep. 2001.

Marshak et al., Strategies for Protein Purification and Characterization, A Laboratory Course Manual, 54-58; 1996.

rProtein A Sepharose TM Fast Flow Instructions; Amersham Bioscience AB; Edition AB; Dec. 2001.

Collins, William E., "Protein Separation with Flow-Through Chromatography", Separation & Purification Reviews, 26:2, 215-253; 1997.

Birch J.R. et al., "Monoclonal Antibodies—Principles and Applications" ISBN 0-471-05147-0, 1st edition; 1995.

Füglistaller, "Comparison of immunoglobulin binding capacities and ligand leakage using eight different protein A affinity chromatography matrices", Journal of Immunological Methods, 124, 171-177; 1989.

Jiskoot et al., "Two-step purification of a murine monoclonal antibody intended for therapeutic application in man Optimisation of purification conditions and scaling up", Journal of Immunological Methods 124, 143-156; 1989.

Knudsen HL et al., "Membrane ion-exchange chromatography for process-scale antibody purification", J. Chromatogr. A 907 : 145-154; 2001.

Racher et al., Manufacture of Therapeutic antibodies, 246-274; 1999.

Roe, S. D., Protein A Leakage from Affinity Adsorbents, AEA Technology, Harwell/Oxon, UK 158 (Separations for Biotechnology 3), 427-32. ISSN:0260-6291, 1994.

Letter from Patrick Mirandah Co. to Lonza Ltd. dated Aug. 11, 2008 and Letter from Indian Patent Office dated Aug. 5, 2008, issued in connection with Indian Patent Application No. 3871/DELNP/2005.

Djuro Josic et al., "Analytical and Preparative Methods for Purification of Antibodies", *Food Technol Biotechnol*, vol. 39, No. 3, 2001, pp. 215-226.

"Rmp Protein A Sepharose Fast Flow—high purity, high throughput, low leakage, low risk", *Downstream Thirty Two* 18-1145-45, 'Online! 2002, XP002357257, Retrieved from the Internet: URL : http://www.jp.amershambiosciences.comlnewsletterldownstreamlpdf/downstream32.p>d fr etried Dec. 1, 2005.

Harish Iyer et al., "Considerations During Development of a Protein A-Based Antibody Purification Process", *Biopharm*, Cleveland, OH, US, vol. 15, No. 1, 2002, pp. 14-16, 18, 20, and 53.

Pete Gagnon, "Affinity Chromatography: The Fine Print", *Validated Biosystems Quarterly Resource Guide for Downstream Processing*, 1999.

Julian Bonnerjea, "Purification of Therapeutic Proteins", *Methods in Molecular Biology* (Clifton, N.J.), 2004, vol. 244, Feb. 2004, pp. 455-462.

"Antibody Purification (Handbook, 18-1037-46, Edition AC)", 2002, *Amersham Bioscience*.

L. O. Narhi et al., "Effect of Three Elution Buffers on the Recovery and Structure of Monoclonal Antibodies", *Analytical Biochemistry*, vol. 253, No. 2, Nov. 15, 1997, pp. 236-245.

Letter & Written Submissions of Lonza Biologics PLC dated Nov. 5, 2008 to Indian Patent Office relating to Indian Patent Application No. 387/DELNP/2005; *Lonza Biologics PLC* vs. *Dr. Reddy's Laboratories*.

Response to Oppositions against EP 1601697 B1 dated Oct. 22, 2008 filed on behalf of Lonza AG.

Letter from Patrick Mirandah Co. To Lonza Ltd. dated May 21, 2009 and Letter from Indian Patent Office dated May 8, 2009, issued in connection with Indian Patent Application No. 3871/DELNP/2005, with Opposition papers attached.

Japanese Office Action dated Oct. 30, 2009, issued in connection with Japanese Patent Application No. 2006-501980.

Jiskoot et al, "Preparation of clinical grade monoclonal antibodies from serum-containing cell culture supernatants", Journal of Immunological Methods, 138 (1991) 273-283.

English translation of Japanese Office Action mailed Aug. 24, 2010, issued in connection with Japanese Patent Application No. 2006-501980.

\* cited by examiner

Fractionation of aggregates across the SP-Sepharose elution peak for high pI antibody

US 7,847,071 B2

ANTIBODY PURIFICATION BY PROTEIN A AND ION EXCHANGE CHROMATOGRAPHY

The present application is a continuation of Ser. No. 11/210,669, filed Aug. 25, 2005 (abandoned), which is a continuation-in-part application of International Application No. PCT/EP2004/002041, filed 1 Mar. 2004, which claims benefit of U.S. Provisional application Ser. No. 60/464,973, filed 24 Apr. 2003, and GB 0304576.2 filed 28 Feb. 2003; Ser. No. 11/210,669 additionally claims benefit of U.S. Provisional application Ser. No. 60/604,464, filed 26 Aug. 2004, the entire contents of each of which is hereby incorporated by reference.

SUMMARY OF THE INVENTION

The present invention relates to the field of antibody purification in biotechnological production. It is an object of the present invention to describe a novel process for purification of such antibody.

Protein A chromatography is widely used in industrial manufacturing of antibodies since allowing for almost complete purification of antibodies, that is usually IgG, in a single step from cell culture supernatants. Protein A affinity columns inevitably are subject to some degree of leakage of ligand from the column upon repeated runs. Partly, this may be due to proteolytic clipping of protein A from the column; in industrial manufacture of antibody for pharmaceutical applications, no protease inhibitor cocktails may be added for regulatory reasons. Unfortunately, this protein A or protein A fragment contaminants retain their affinity for IgG and are difficult to remove from the purified antibody due to ongoing complex formation. Removal is mandatory since protein A which is a bacterial protein will elicit an unwanted immune response; further, model complexes formed by adding protein A to monomeric IgG have been reported to activate Fc-bearing leukocytes and the complement system to generate oxidant and anaphylatoxin activity in vitro (Balint et al., Cancer Res. 44, 734, 1984).

The commercialisation of recombinant Protein A species as set forth in U.S. Pat. No. 6,399,750 which recombinant species is attached to the column matrix via a single thioester bond allowed for higher capacity protein A columns. As a concomittant disadvantage, the leakage rate of such recombinant Protein A matrices is often drastically increased in contrast to many traditional, multi-point attached natural Protein A matrices obtained by CNBr coupling. Protein A contaminant removal should therefore proceed without concomitant removal of complexed IgG.

Balint et al. (ibd.) demonstrated that such IgG-Protein complexes can be separated from uncomplexed IgG by gel filtration. Low through-put and loss in antibody yield are the disadvantages of this method.

U.S. Pat. No. 4,983,722 teaches selective separation of contaminating protein A from a protein-A purified antibody preparation by absorbing the mixture to an anion exchanger material and to separate both components by sequentially eluting the antibodies and protein A under conditions of increasing ionic strength. This resolution method is highly dependent on the pI of the antibody which is specific and highly variable for a given antibody. Further, throughput is limited by the steepness of the salt gradient required for obtaining separation.

DETAILED DESCRIPTION OF THE INVENTION

Figure 1:
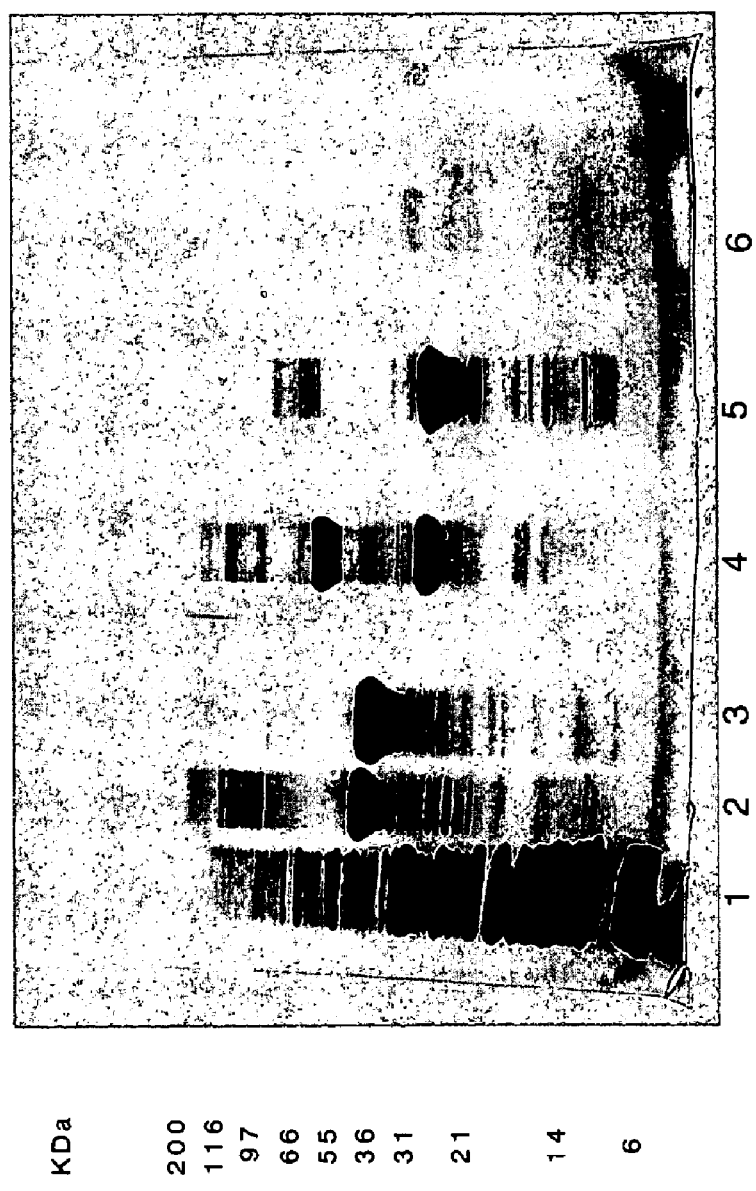
FIG. 1 shows the result of pretreatment by means of non-reducing 10% SDS-PAGE for a staphylococcal protein A standard (lane 1: native protein A; lane 2: after pretreatment) and pure, uncoupled Streamline™ recombinant protein A (provided by courtesy of Pharmacia, now Amersham-Biosciences; lane 4: native recombinant protein A; lane 5: after pretreatment).

It is an object of the present invention to devise another method for separating protein A or protein A fragments from antibody, preferably an IgG, which method avoids the disadvantages of the prior art. According to the present invention, such object is solved according to the independent claims 1 and 9.

According to the present invention, a method of purifying an antibody is devised which method comprises the steps of: firstly, purifying an antibody by means of protein A affinity chromatography wherein the protein A is a native protein A or a functional derivative thereof.

Secondly, loading the purified antibody on an ion exchange material under conditions which allow for binding of the protein A or its functional derivative and thirdly, collecting the antibody, preferably collecting at least 70%, more preferably collecting at least 80%, most preferably collecting at least 90% of the amount of antibody loaded onto the ion exchange material in the flow-through of the ion exchanger whilst any contaminant protein A or protein A derivative is bound to the ion exchange material.

Protein A is a cell surface protein found in Staphylococcus aureus. It has the property of binding the Fc region of a mammalian antibody, in particular of IgG class antibodies. Within a given class of antibodies, the affinity slightly varies with regard to species origin and antibody subclass or allotype (reviewed in Surolia, A. et al., 1982, Protein A: Nature's universal 'antibody', TIBS 7, 74-76; Langone et al., 1982, Protein A of staphylococcus aureus and related immunoglobulin receptors, Advances in Immunology 32:157-252). Protein A can be isolated directly from cultures of S. aureus that are secreting protein A or is more conveniently recombinantly expressed in E.coli (Lofdahl et al., 1983, Proc. Natl. Acad. Sci. USA 80:697-701). Its use for purification of antibodies, in particular monoclonal IgG, is amply described in the prior art ( e.g. Langone et al., supra; Hjelm et al, 1972; FEBS Lett. 28: 73-76). For use in protein A affinity chromatography, protein A is coupled to a solid matrix such as crosslinked, uncharged agarose (Sepharose, freed from charged fraction of natural agarose), trisacryl, crosslinked dextrane or silica-based materials. Methods for such are commonly known in the art, e.g. coupling via primary amino functions of the protein to a CNBr-activated matrix. Protein A binds with high affinity and high specificity to the Fc portion of IgG, that is the Cγ2-Cγ3 interface region of IgG as described in Langone et al., 1982, supra. In particular, it binds strongly to the human allotypes or subclasses IgG1, IgG2, IgG3 and the mouse allotypes or subclasses IgG2a, IgG2b, IgG3. Protein A also exhibits an affinity for the Fab region of immunoglobulins that are encoded by the $V_H$ gene family, $V_H$ III (Sasso et al., 1991, J. Immunol, 61: 3026-3031; Hilson et al., J Exp. Med., 178: 331-336 (1993)). The sequence of the gene coding for protein A revealed two functionally distinct regions (Uhlen et al., J. Biol. Chem., 259: 1695-1702 (1984); Lofdahl et al., Proc. Nutl. Acad. Sci.(USA), 80: 697-701 (1983)). The amino-terminal region contains five highly homologous IgG-binding domains (termed E, D, A, B and C), and the carboxy terminal region anchors the protein to the cell wall and membrane. All five IgG-binding domains of protein A bind to IgG via the Fc region, involving e.g. in human IgG-Fc residues 252-254, 433-435 and 311, as shown for the crystal structure in Deisenhofer et al. (1981, Biochemistry 20: 2361-2370) and in Sauer-Eriksson et al. (1995, Structure 3: 265-278) in case of the B-domain of protein A. The finding of two essentially contiguous main binding sites in the Fc portion has been confirmed in the NMR-solution study of Gouda et al., 1998, Biochemsitry 37: 129-136. In principle, each of the IgG-binding domains A to E of protein A is sufficient for binding to the Fc-portion of an IgG.

Further, certain alleles of the VH3 family in man have been found to mediate optionally binding of human Ig by protein A (Ibrahim et al., 1993, J. Immunol. 151:3597-3603; V-region mediated binding of human Ig by protein A). In the context of the present application, in another, separate object of the present invention, everything that has been said applying to Fc-region binding of antibody to protein A applies likewise to the binding of antibodies via such VH3 family protein A-binding allele in case that the Fc-region of such antibody did not allow on itself for high-affinity protein A binding. It may be considered an equivalent embodiment of the prinicipal, Fc-based method of the present invention; the latter is further described in the subsequent sections.

An IgG antibody according to the present invention is to be understood as an antibody of such allotype that it can be bound to protein A in a high-affinity mode. Further, apart from the Fc portions of the antibody that are relevant for binding to protein A, such antibody must not correspond to a naturally occuring antibody. In particular in its variable chain regions portions, it can be an engineered chimeric or CDR-grafted antibody as are routinely devised in the art. An IgG-antibody according to the present invention is to be understood as an IgG-type antibody, in short.

A functional derivative of protein A according to the present invention is characterized by a binding constant of at least $K=10^{-8}$ M, preferably $K=10^{-9}$ M for the Fc portion of mouse IgG2a or human IgG1. An interaction compliant with such value for the binding constant is termed 'high affinity binding' in the present context. Preferably, such functional derivative of protein A comprises at least part of a functional IgG binding domain of wild-type protein A which domain is selected from the natural domains E, D, A, B, C or engineered muteins thereof which have retained IgG binding functionality. An example of such is the functional 59 aminoacid 'Z'-fragment of domain B of protein A which domain may be used for antibody purification as set forth in U.S. Pat. No. 6,013,763. Preferably, however, an antibody binding fragment according to the present invention comprises at least two intact Fc binding domains as defined in this paragraph. An example of such are the recombinant protein A sequences disclosed e.g. in EP-282 308 and EP-284 368, both from Repligen Corporation.

Alone or in combination with a protein A or a functional protein A-fragment or derivative as defined in the preceding sections, further preferred are protein A fragments that are engineered to allow of single-point attachement. Single point attachment means that the protein moiety is attached via a single covalent bond to a chromatographic support material of the protein A affinity chromatography. Such single-point attachment by means of suitably reactive residues which further are ideally placed at an exposed amino acid position, namely in a loop, close to the N- or C-terminus or elsewhere on the outer circumference of the protein fold. Suitable reactive groups are e.g. sulfhydryl or amino functions. More preferably, such recombinant protein A or functional fragment thereof comprises a cysteine in its amino acid sequence. Most preferably, the cysteine is comprised in a segment that consists of the last 30 amino acids of the C-terminus of the amino acid sequence of the recombinant protein A or functional fragment thereof. In a further preferred embodiment of such type, the recombinant protein A or functional fragment thereof is attached by at least 50% via a thioether sulphur bond to the chromatographic support or matrix material of the protein A-affinity chromatography medium. An example of such an embodiment is described e.g. in U.S. Pat. No. 6,399,750 from Pharmacia and is commercially available under the brandnames of Streamline™ or MabSelect™ from Amersham-Biosciences, depending on the nature of the support matrix used. In the present context, thioether is to be understood narrowly as a —S— bonding scheme irrespective of chemical context, deviating in this regard from normal chemical language; it is possible, for instance, that said —S— 'thioether' bridge according to the present invention is part of a larger functional group such as e.g. a thioester or a mixed acetal, deviating in this regard in the context of the present application from the reacitivity-based normal language of chemists. Preferably, the thioether bridge is a thioether bridge in its ordinary, narrow chemical meaning. Such bridging thioether group can be e.g. generated by reacting the sulfhydryl-group of a cysteine residue of the protein A with an epoxide group harbored on the activated chromatographic support material. With a terminal cysteine residue, such reaction can be carried out under conditions suitable as to allow only for coupling of an exposed, unique sulfhydrylgroup of a protein as to result in single-point attachment of such protein only.

In a particularly preferred embodiment, the protein A or functional protein A derivative according to the present invention is the recombinant protein A disclosed in U.S. Pat. No. 6,399,750 which comprises a juxtaterminal, engineered cysteine residue and is, preferably by at least 50%, more preferably by at least 70%, coupled to the chromatographic support material through the sulphur atom of said cysteine residue as the sole point of attachment. Further preferred, such coupling has been achieved by means of epoxide mediated activation, more preferably either by means of 1,4-bis-(2,3-epoxypropoxy) butane activation of e.g. an agarose matrix such as Sepharose Fast Flow (agarose beads crosslinked with epichlorohydrin, Amersham Biosciences, UK) or by means of epichlorohydrin activation of e.g. an agarose matrix such as Sepharose FF. Further preferred in combination with aforesaid preferred embodiment according to this paragraph is that the first ion exchanger is an anion exchanger, in particular a quaternary amine-based anion exchanger such as Sepharose Q™ FF (Amersham-Biosciences/Pharmacia), most preferably it is an anion exchanger having the functional exchanger group Q coupled to a matrix support which group Q is N,N,N-Trimethylamino-methyl, most preferably the anion exchanger is Sepharose Q™ FF from Pharmacia/Amersham Biosciences. The quarternary amino group is a strong exchanger which further is not susceptible to changes in pH of the loading/wash buffer. The fast flow exchanger matrix is based on 45-165 µm agarose beads having a high degree of crosslinking for higher physical stability; further sepharose is devoid of the charged, sulfated molecule fraction of natural agarose and does not allow for unspecific matrix adsorption of antibody, even under condition of high antibody loads. An example of such an embodiment can be found in the experimental section.

A contaminant protein A according to the present invention is any type of functional, IgG binding offspring of a protein A or a functional derivative thereof as defined above which is obtained upon eluting bound antibody from a protein A affinity chromatography column. Such contaminant protein A species may result e.g. from hydrolysis of peptide bonds which is very likely to occur by means of enzyme action in particular in industrial manufacturing. Protein A chromatography is applied as an early step in downstream processing when the crudely purified, fresh product solution still harbors considerable protease activity. Dying cells in the cell culture broth or cells disrupted in initial centrifugation or filtration steps are likely to have set free proteases; for regulatory purposes, supplementation of the cell culture broth with protease inhibitors prior or in the course of downstream processing is usually not accomplished, in contrast to biochemical research practice. Examples are Phenyl-methyl-sulfonyl-chloride (PMSF) or $\epsilon$-caproic acid. Such chemical agents are undesirable as an additives in the production of biopharmaceuticals. It is further possible that recombinant functional derivatives or fragments of protein A are less protease resistant than wild-type protein A, depending on the tertiary structure of the protein fold. Amino acid segments linking individual IgG binding domains might be exposed once the total number of binding domains is reduced. Interdomain contacts may possible contribute to the stability of domain folding. It might also be that binding of antibody by protein A or said functional derivatives thereof influences or facilitates susceptibility to protease action, due to conformational changes induced upon binding of the antibody. Again, wild-type or full length protein A or functional, engineered fragments thereof might behave differently. Preferably, contaminant protein A according to the present invention still is functional, IgG binding protein and thus is associated with the protein A-purified antibody when loaded onto the subsequent ion exchange separation medium according to the present invention. The high-affinity based association of contaminant protein A with the purified antibody is the reason why it is difficult to efficiently separate contaminant protein A from purified antibody.

Preferably, according to the present invention the antibody sought to be purified is harvested from a cell culture prior to purifying the antibody be means of protein A affinity chromatography. More preferably, said cell culture is a mammalian cell culture. Mammalian cells have large compartments called lysosomes harboring degradating enyzmes which are disrupted upon cell death or harvest. In particular, said cell culture may be a myeloma cell culture such as e.g. NSO cells (Galfre, G. and Milstein, C. Methods Enzymology, 1981, 73, 3). Myeloma cells are plasmacytoma cells, i.e. cells of lymphoid cell lineage. An exemplary NSO cell line is e.g. cell line ECACC No. 85110503, freely available from the European Collection of Cell Cultures (ECACC), Centre for Applied Microbiology & Research, Salisbury, Wiltshire SP4 0JG, United Kingdom. NSO have been found able to give rise to extremly high product yields, in particular if used for production of recombinant antibodies. In return, NSO cells have been found to give reproducibly rise to much higher levels of contaminant protein A than other host cell types at least with certain protein A affinity chromatography systems employing recombinant, shortened fragments of wild-type protein A which recombinant protein A is possibly single-point attached protein A. An example of such is Streamline™ rProtein A affinity chromatography resin (Amersham Biosciences; essentially thioester single-point attached recombinant protein A as described in U.S. Pat. No. 6,399,750). Levels of about or in excess of 1000 ng contaminant protein A/mg antibody could be obtained with Streamline™ rProtein A affinity columns. The method of the present invention distinguishes from the prior art in efficiently reducing contaminant protein A from such elevated levels to <1 ng/mg antibody in a single, fast purification step, that is with a purification factor of about 1000x.

Further preferred is, alone or in combination with the preceding paragraph, that the antibody that is to be purified by means of protein A affinity chromatography is not treated as to inactivate proteases at or after harvest, more preferably is not in admixture with at least one exogenously supplemented protease inhibitor after harvest. Most preferably, said protease inhibitor is selected from the group consisting of PMSF, specific proteinase inhibiting peptides as described in Laskowski et al., 1980, Protein inhibitors of proteinases, Ann. Rev. Biochem. 49, 593-626, and epsilon-caproic acid.

Operation of protein A affinity chromatography has been widely described in the technical literature and does not need to be further described. Another example apart from the above cited is e.g. Duhamel et al., J. Immunological Methods 31, (1979) 211-217, pH Gradient elution of human IgG1, IgG2 and IgG4 from protein A-Sepharose.

Preferably, the contaminant protein A is reduced to a concentration of <10 ng/mg antibody, more preferably <4 ng/mg antibody, most preferably <1 ng/mg antibody in the flow-through of the first ion-exchanger, wherein antibody is preferably to be understood as to refer to IgG. The Elisa assay method for validation of these threshold values is described in detail in the experimental section; it should be noted that acidification of the sample to a pH $\leqq 4$, preferably in the presence of a mild detergent, is crucial for accurate determination of the amount of leaked protein A. It goes without saying that his is threshold is to be understood such as that the loading capacity of the first ion-exchanger for protein A binding is never exceeded, leading inevitably to break-through of contaminant protein A. A suitable Elisa-based method for assaying protein A or protein A fragments is described in U.S. Pat. No. 4,983,722. Suitable anti-protein A antibodies are commercially available, e.g. from Sigma-Aldrich. In particular when using derivatives of protein A which derivatives have been engineered to harbor additional sulfhydryl groups, proper maintenance of the protein standard is important. It may be important to verify the monomeric character of such pure protein A derivative used as a standard for quantification of the test sample, since covalent di- or multimers formed via —S—S— bridges could lead to wrong results. Verification can be easily achieved by SDS-PAGE analysis under reducing and non-reducing conditions, as is customary in the art. Reduction of such protein A derivative- standard solution by means of DTT or beta-mercaptoethanol helps accordingly to circumvent errors of measurement in the ELISA-technique.

Further preferred, in the method according to the present invention at least 70%, more preferably at least 80%, most preferably at least 90% of the antibody loaded onto the first ion exchanger can be recovered in the flow-through of the ion-exchanger. Preferably, and disregarding glycoforms and eventual processing variants of the same antibody, there is only type of species antibody present in the mixture that is going to be purified by means of protein A affinity and subsequent ion exchange chromatography according to the present invention. For instance, when purifying a human or human-mouse or primate or primatized IgG antibody according to the present invention, no bovine IgG as may be carried over from serum in serum-supplemented cell culture is present. To put it differently, preferably the method of the present invention is applied to curde, unpurified antibody harvested from serum-free cell culture.

The first ion exchanger according to the present invention is an anion exchanger resin; protein A can be bound by both types of resin as described (EP-289 129 B1). The first ion exchanger or anion exchanger can be operated in the column mode at a certain flow rate or in batch operation mode, by submerging the ion exchange resin into the mildly agitated sample solution and further exchanging liquid media by filtration subsequently. According to the present invention and taking into account the pI of a given antibody, it is possible to define suitable conditions of pH and ionic strength for loading the first ion exchanger, which conditions result in retaining the antibody in the flow through whilst the protein A contaminant is bound and thus removed from the antibody. As has been said before, the method according to the present invention allows of faster separation of antibody from contaminant protein A. Examples of functional groups of such first, anion exchanger that are attached to a matrix support are e.g. primary, secondary, and particularly tertiary or quaternary animo groups such as aminoethyl, diethylaminoethyl, trimethylaminoethyl, trimethylaminomethyl and diethyl-(2-hydroxypropyl)-aminoethyl. Suitable chromatographic support matrixes for the anion exchanger are known in the art. Examples are agarose-based resins and beads, dextran beads, polystyrene beads and polystyrene/divinyl-benzene resins. Most preferably, the ion exchanger is a quaternary amine-based anion exchanger mounted on an agarose matrix such as e.g. Sepharose CL-6B or Sepharose Fast Flow (FF) from Amersham-Biosciences/Pharmacia. An example of such is Sepharose Q™ from Amersham-Biosciences/Pharmacia. Further preferred in conjunction with the use of a first anion exchanger is that the antibody according to the present invention is a monoclonal antibody that has an isoelectric point (pI) which is at least two pH units above, that is it is more basic than, the pI of the protein A used in the preceding protein A affinity chromatography step; e.g. whereas native protein A has a pI of about 5.0, Streamline recombinant protein A has a pI of about 4.5. Preferably, the antibody according to the present invention is a monoclonal antibody that has an isoelectric point (pI) which is at least 6.5 or above, more preferably is 7.0 or above, most preferably has an pI of at least 7.5 or above. It should be noted that this refers to the pI of the actually harvested and purified antibody, not the pI that can be simply predicted from the amino acid sequence alone. The actually purified antibody molecule may have undergone further modifications of the polypeptide backbone such as glycosylation, which modifications may add charged moieties and thus may have changed the pI of the molecule. Upon determination of pI for product antibody by means of isoelectric focusing (IEF), the microheterogenity of posttranslational processing of the antibody protein, e.g. a monoclonal antibody protein, leads to a wider pI-range for individual product antibody glycoprotein molecules, them resembling a smear in an IEF gel rather than a single band and thus a specific numeric value for at least the majority of product. According to the present invention, in such afore mentioned preferred embodiment, the 'pI of an antibody' refers to that share of antibody product molecules whose pI is within the preferred range of pI as specified above. All further definitions of this description, such as the %-proportion of antibody recovered after a given purification step, refer to said pI-compliant share of antibody only.

Preferably, the pH of buffer used for loading and running the first ion exchanger is set as to put opposing total charge on the antibody and the protein A or protein A contaminant to be separated by means of the ion exchanger in a flow-through mode according to the present invention, taking the pI's of antibody and protein A or protein A derivative into account. However, this does pertain to average pI value as determinable by experimental means; hence having regard to glycoforms of antibodey, this doesn't mean that a smaller share of glycoforms might be close or be at pI. According to the present invention, it is less desirable to use a buffer pH set at the pI of either of these in view of optimum recovery of antibody and separation from contaminant protein A.

The mode of operation of a first anion exchanger according to the present invention requires buffer exchange of the acidic or neutralized eluate from the protein A affinity chromatography step with the equilibration buffer of the first anion exchanger. Equilibration buffer and loading buffer are identical in the method of the present invention. Commonly employed ultrafiltration devices such as sold by Amicon or Millipore can be expediently used for that purpose; those avoid the dilution effects whilst using e.g. low molecular weight porous filtration matrices such as Sephadex G-25. The equilibration buffer according to the present invention preferably has a salt concentration of a displacer salt such as e.g. sodium chloride in the range of 1 to 150 mM, more preferably of from 5 to 110 mM, most preferably of from 20 to 100 mM salt. The pH of the equilibration buffer is preferably in the range of pH 6.5 to pH 9.0, more preferably is in the range of pH 7.5 to pH 8.5, most preferably is in the range of pH 7.9 to pH 8.4. It should be kept in mind that N-terminal amino function of a protein has a pKs value of about 9.25, thus binding of contaminant protein A and any other already negatively charged protein to an anion exchanger will get stronger at more basic pH; for a given application, the pH of the loading buffer might need finetuning for optimal discrimination of binding and non-binding for a given pair of antibody and contaminant protein A having differing pI values and different content of cysteine and histidine side chains which may contribute to changes in charge within the selected ranges of pH. Further, a more basic pH interferes with proteinA-antibody interactions as will do any increase in ionic strength; likewise, ionic strength needs finetuning to balance prevention of binding of antibody with the need to abolish binding of contaminant protein A. It goes without saying for the skilled artisan that the ionic strength of the buffer is usually inversely correlated with the pH value; the more strongly protein A gets bound to the anion exchanger depending on pH, the more salt is tolerated for preventing binding of antibody and for interfering with potential proteinA-antibody interactions. Thus, the above given ranges for pH and displacer salt thus are to be understood as to be correlated: The lower the pH, the less salt is found permissible within the above given preferred ranges for working the invention. Further salt freight is added by the pH buffering substance, further increasing the ionic strength of the solution. The ionic strength can be determined by measuring the conductivity of the equilibration buffer. The term 'conductivity' refers to the ability of an aqueous solution to conduct an electric current between two electrodes measures the total amount of ions further taking charge and ion motility into account. Therefore, with an increasing amount of ions present in the aqueous solution, the solution will have a higher conductivity. The unit of measurement for conductivity is mS/cm (milliSiemens/cm), and can be measured using a commercially available conductivity meter, e.g. from Topac Inc. (Hingham, Mass./U.S.A.) or Honeywell. In the context of the present application, all numerical values pertain to the specifc conductivity at 25° C. Preferably, the loading or equilibration buffer for the first anion exchange step has a conductivity 0.5-5 mS/cm, more preferably of from 1-3 mS/cm, most preferably of from 1.25-2.5 mS/cm. Ideally, it has a conductivity of about 2 mS/cm. Examples of suitable buffer salts can be found in Good, N. E. (1986, Biochemistry 5:467-476). E.g. Tris.HCl buffer or a sodium hydrogen phosphate buffer as customarily employed are suitable buffering substances. The concentration of the buffer substance is customarily in the range of e.g. 10-40 mM buffer salt. Amongst potential anion species useful for devising a buffer, those having lower specific strength of anion elution as compared to chloride, which property of low elution strength is approximately inversely correlated with the density of ionic charge and is approximately proportional to the ionic size, are preferred. Empirical comparisons of strength of anionic elution are tabulated in the standard textbooks of biochemistry. More preferably, the buffer substance according to the present invention is a phosphate buffer. Hydrogenphosphate has a low elution strength, in particular if employed at a pH at or below pH 8, and further excels by particularly low chaotropic properties.

In a further preferred embodiment, the first anion exchanger is a ceramic matrix-anion exchanger such as the Biosepra-branded HyperD® anion exchangers, more preferably a ceramic matrix-anion exchanger having a quaternary ammonium (=quaternary amine-based) ionic, matrix bonded functional group. These are extremly useful for purification at a therapeutic scale. Most preferably, the quaternary, ceramic anion exchanger is a Q-ceramic matrix anion exchanger such as, and particularly preferred, the Q-HyperD® anion exchanger resin sold by Ciphergen Biosystems Ltd., Guildford/Surrey, UK under the 'Biosepra' trademark. The above and below mentioned preferred embodiments on pI of antibody, protein load and buffer pH are also preferred in combination with this embodiment, with the exception of the preferred conductivity of buffer when using Q-Hyper D® material being at best 0.5-2 mS/cm, more preferably being in the range of 0.6-1.7 mS/cm, most preferably at about 1 to 1.5 mS/cm and in particular when using Q-Hyper D®-F ion exchanger. This conductivity ensures best purification result in view of deriching contaminant protein A or fragments thereof from the product protein. The Ceramic HYPERD sorbents are made using a rigid porous bead, which is coated and permeated with a functionalized hydrogel. This gives the beads outstanding rigidity and flow performance, as well as exceptional mass transfer and dynamic properties. The Ceramic HYPERD sorbents are very easy to use. Their relatively high density makes them easy to pack and use in very large columns. The complete lack of shrinking or swelling eliminates the need for repeated packing/unpacking of columns. Today, columns in excess of 500 liters are used for preparative chromatography of molecules for therapeutic use. The Ceramic HYPERD ion exchangers are also available in a 50 µm grade (F grade) for preparative processes, with their high capacity and lower back pressure the 50 grade is perfect for capture processes and general downstream processing. The ceramic nature of the bead makes it chemically very stable and it can be cleaned using most commonly used cleaning agents, including 0.5 M NaOH.

Whereas batch mode operation is possible, column operation mode is preferred for the first anion exchanger step. In that case, a flow rate of about 10 to 60 ml/h can be advantageously employed. The loading concentration of antibody loaded can favorably be in the range of 10 to 30 mg antibody/ml exchange resin. It goes without saying that the use of extremly diluted samples would give rise to decreased yield of antibody, as is known to the skilled person. The antibody sought to be purified is collected in the low-through of the loading operation including about one column volume of wash with the same equilibration buffer. The pH of the flow-through may be adjusted to neutral pH for improving stability and preventing aggregation and/or precipitation of antibody protein.

After the first anion exchanger, the antibody is ready for use in applications or may be deemed to require further polishing by customary purification methods. In a further preferred embodiment, the first ion exchange step is followed by a second ion exchange step in which second step the antibody is loaded and bound by the second ion exchange medium and is eluted with a buffer other than the loading buffer, by means of increased salt and/or pH, as an essentially monomeric, non-aggregated antibody. 'Essentially' means less than 5% in this context. Preferably, alone or in combination with a preferred embodiment described in the preceding sections, the second ion exchanger is a cation exchanger. Such combination of a protein A chromatography step followed by a first anion exchanger and a second cation exchanger step is novel. It is well known that most trace contaminant proteins from cell culture broth have much lower pI values than antibodies, in particular IgG antibodies; cation exchange will therefore allow of efficient removal both of aggregated antibody and potential infectious agents such as virus capsids as well as of protein contaminants other than antibody. Due to speedy operation, highly efficient recovery of antibody after loading, binding to and elution from the co and high capacity of loading, it allows also of repeated, cyclic operation with a single batch of antibody with additive effect of the purification factor achieved in a single round of binding and elution. Preferably, the pH of the loading buffer is about pH 4 to 7, more preferably pH 4.01 to 6, most preferably pH 4.02 to 5.5. Further preferred, the the antibody is eluted from the cation exchanger with a salt gradient in the range of from 0.1 to 1.2 M salt, wherein the salt preferably is an alkaline metal salt, more preferably a lithium, potassium or sodium salt. Preferably, elution takes place at a pH of from pH 7 to 8 in order to have maximum aggregate removal and minimal damage to antibody due to acidic conditions. Optionally preferred, the elution takes place at a an acid pH of from pH 4 to 7, more preferably 4.01 to 6 for maximizing removal of contaminant protein A; levels as low as <0.4 ng/mg antibody can be realized in this way. This second cation exchanger step renders traditional gel filtration moot whilst allowing of high-capacity as well as fast operation as is typical for ion exchangers. Ion exchangers support loads of 10-30 mg antibody/ml resin. In a particularly preferred embodiment, the purification method of a first anion exchanger and a second cation exchanger step in the aftermath of protein A chromatography renders clinical grade antibody in the absence of a further, terminal size exclusion chromatography (SEC) step which SEC step would have a molecular weight cut off suitable for separating antibody aggregates and/or antibody-protein A complexes from monomeric antibody such as an normal IgG.

On a general note, the method of the present invention can not be exploited for antibodies that have been raised against protein A-borne epitopes. Such antibodies are disclaimed, though this is an obvious limitation to the skilled artisan.

The most appealing feature of the method of the present invention is that purifying antibody via an anion exchanger in a non-binding or flow-through mode, the capacity of the column is not all limiting the through-put of material; the capacity is only decisive with regard to minor amounts of contaminant protein A retain. This saves a lot of processing time and material resources whilst allowing for very efficient removal of protein A contaminant.

Experiments

1. Protein A Elisa

Numerous Elisas for testing of protein A or recombinant protein A have been described (see U.S. Pat. No. 4,983,722 and references described in there). For all work described below, a simple sandwich Elisa was used in which capture anti-protein A antibody coated on a flat-bottomed 96 well microtiter plate (Nunc™) retains the protein A. Bound protein A is then detected an a biotinylated anti-protein A detection antibody, which allows for further binding of streptavidin conjugated horseradish peroxidase (Amersham #RPN 1231). Commercially available anti-protein A rabbit antibody (raised against the natural S. aureus protein A) for capture is available from Sigma-Aldrich (#P-3775). It was this antibody which was used through-out this study. The detection rabbit antibody was equally purchased from Sigma-Aldrich (#3775). After coating the protein by unspecific adsoprtion process, the coated protein is used to retain protein A-specific protein A capture antibody which capture antibody is further detected with bioinylated rabbit anti-protein A and streptavidin-horseradish peroxidase. Tetramethyl benzidine is used as the chromogenic substrate. Samples of unknown concentration are read off against a standard curve using the very parent-protein A or -protein A derivative of the contaminant protein A sought to be detected. Coating at acidic pH as well as proper preparation of the standard has proven important. In particular for recombinant protein A's engineered to carry additional cysteine residue such as e.g. Streamline protein A™ (Amersham Biosciences, formerly Pharmacia), the standard solution was found to require pretreatment with a reducing sulfhydryl agent to ensure monomeric state of the protein standard solution.

Wild-type protein A standard, in contrast, is commercially available from a number of companies, e.g. Sigma-Aldrich/Switzerland (#P6031) or Pharmacia (#17-0770-01) and does not require such pretreatment. For the below described experiments observing leakage of contaminant protein A from Streamline™ matrix, samples of unconjugated recombinant protein A obtained from the manufacturer were used as a standard.

1.1 Pretreatment of Cys-enriched Protein A-standard

Pure recombinant protein A-Cys as commercially in the Streamline™ protein A affinity chromatography (Amersham Biosciences) column material was obtained freeze-dried from Pharmacia/Amersham Biosciences. Up to 20 mg/ml protein were dissolved in 0.1M Tris pH 8 containing 0.5 M NaCl, 1 mM EDTA and 20 mM dithioerythritol, incubated for 15-30 min. at room temperature and desalted with a disposable PD-10 gel filtration column (Amersham Biosciences). All buffers used for handling the standard solution before coating should be $N_2$-treated to prevent oxidation of the thiol groups. Preparation of the protein standard was carried out at best immediately prior to use of the standard for coating the microtiter plates. Optionally, a 1 mg/ml stock solution was prepared and kept at −65° C. in a freezer; after thawing, monomeric character of protein A was assayed from an aliquot loaded on non-reducing SDS-PAGE. The concentration of protein standard was determined by Bradford assay (Bradford et al., 1976, Anal. Biochem. 72:248-254; Splittgerber et al., 1989, Anal. Biochem. 179:198-201) as well as by automated amino acid analysis. The result of such pretreatment is shown in FIG. 1 by means of non-reducing 10% SDS-PAGE for a staphylococcal protein A standard (lane 1: native protein A; lane 2: after pretreatment) and pure, uncoupled Streamline™ recombinant protein A (provided by courtesy of Pharmacia, now Amersham-Biosciences; lane 4: native recombinant protein A; lane 5: after pretreatment). Lane 1 is a molecular weight marker with the corresponding molecular masses being denoted on the vertical axis. The recombinant protein A from Pharmacia harboring an additional Cys residue shifts after reduction to lower molecular weight; a monomeric band at about 34 kD is preserved and much more intense, stemming obviously from dissociation of disulfide bridged dimers.

1.2 Elisa 1.2.1 Preparation of Sample

By two dilution steps, 1:200.000 dilution of the 1 mg/ml protein A standard stock solution was prepared to provide the top standard at 50 ng/ml. Thereof, dilutions down to 0.2 ng/ml were prepared for assaying the standard curve. Further, the dilutions of the standard ('spinking solutions') were used for spiking of duplicate product samples to be tested in order to exclude presence of interfering substances in the sample.

For final product sample testing, every sample is divided into 2 equal volumes of 500 µl. One is spiked with the 1000 ng/ml spiking solution, or the 10 pg/ml solution if appropriate, to give a final protein A content of 10 ng protein A per mg of antibody. The other half is spiked with the same volume of sample buffer; thus the dilution factor of the product sample due to spiking is accounted for. Both types of preparation will be referred to as 'spiked sample' in the following. The sample buffer was made up from 7.51 g Glycine (base), 5.84 g NaCl, 0.5 ml Triton X-100 to a volume of 1 L with deionized or bidestillated water.

For optimal accuracy measurements, the antibody concentrations in the samples were pre-determined by customary Elisa's well known in the art. A further standard solution was spiked with an equal amount of a known standard antibody of comparable constant region affinity for protein A, to determine efficiency of the acidification step and to unravel any potential systematic error introduced by antibody binding to and thus scavenging protein A from capture in the assay.

Acidification: To 450 µl of spiked sample or standard is added 200 ul of 0.2 M citrate/0.05% Triton X-100 buffer at pH 3.0. All samples were done in triplicate. Further, dilutions of sample were prepared and tested in triplicate since the assay works optimal for antibody concentrations being in the range of 1 mg/ml and 0.2 mg/ml. The acidification step is crucial in the present assay to liberate contaminant protein A or A fragments which were otherwise bound to the excess of antibody present in the sample solution.

1.2.2 Coating of Microtiter Plates with Antibody

Coating buffer was made up from 1.59 g/L Na2CO3, 2.93 g/L NaHCO3 and 0.20 g/L sodium azide. The pH of the buffer was adjusted to pH 9.6. Add 100 µl antibody solution per well comprising antibody in an amount sufficient as not to show saturation for the protein A standard. Cover plate with plastic film and place in humidity chamber. Incubate at 37° C. overnight for approximately 18 hours. Rinse all wells 3 times with at least 300 µl washing buffer [NaCl 5.8 g/L, $Na_2HPO_4$ 1.15 g/L, $NaH_2PO.H_2O$ 0.26 g/L, EDTA 3.7 g/L, Tween-20 0.2 g/L, butanol 10 ml/L, pH 7.2], and tap dry. Add 250 µl blocking buffer [coating buffer with 0.5% casein hammarsten] to each well and incubate for 2 hours at ambient temperature on a benchtop orbital shaker (speed 120 rpm). Rinse all wells three times with at least 300 µl washing buffer, and tap dry.

1.2.3 Incubation of Sample and Detection

Plate out standards and samples including any spiked samples with 100 µl /well. Cover plate with plastic film and incubate for 90 minutes at ambient temperature on an orbital benchtop shaker. Rinse all wells three times with at least 300

μl washing buffer, and tap dry. Dilute biotinylated rabbit anti-protein A at the previously determined optimal dilution. Add 100 μl/well, cover plate with plastic film and incubate for 90 minutes at ambient temperature on an orbital shaker. Repeat rinsing.

Dilute strepavidin-horseradish peroxidase at the previously-determined optimal dilution using conjugate buffer [Na2HPO4 1.15 g/L, NaCl 5.84 g/L, NaH2PO4.H20 0.26 g/L, EDTA 3.73 g/L, Triton X-100 0.05% (v/v), pH 7.2]. Add 100 μl/well, cover plate in plastic film and incubate for 45 minutes at ambient temperatur on an orbital shaker. Repeat rinsing. Add 100 μl freshly-prepared tetramethyl-benzidine (TMB, ICN product number #980502) substrate solution. The substrate solution is prepared like this: A stock solution is prepared by dissolving 10 mg TMB in 1 ml DMSO. 10 μl of that stock, further 10 μl of $H_2O_2$ are added to a 2.05 % (w/w) sodium acetate aequeous solution that was adjusted to pH 6.0 with 0.5 M citric acid. It goes without saying that all water used for preparing any reagent of the assay is of highest quality, that is deionized ultrapure or at least bidestillated water.

The substrate solution is incubated at ambient temperature for 8-11 minutes on a shaker. The reaction is then stopped by adding 50 μl per well of stopping solution [13% $H_2SO_4$]. Within 10 min. after addition of the stopping solution, the absorbance of the wells at wavelength 450 nm is determined on a plate-reading spectrophotometer.

The detection limit for such Elisa is 0.2 ng/ml Protein A, with a working range of from 0.2 to 50 ng/ml. The interassay variability is less than 10%.

Figure 2:
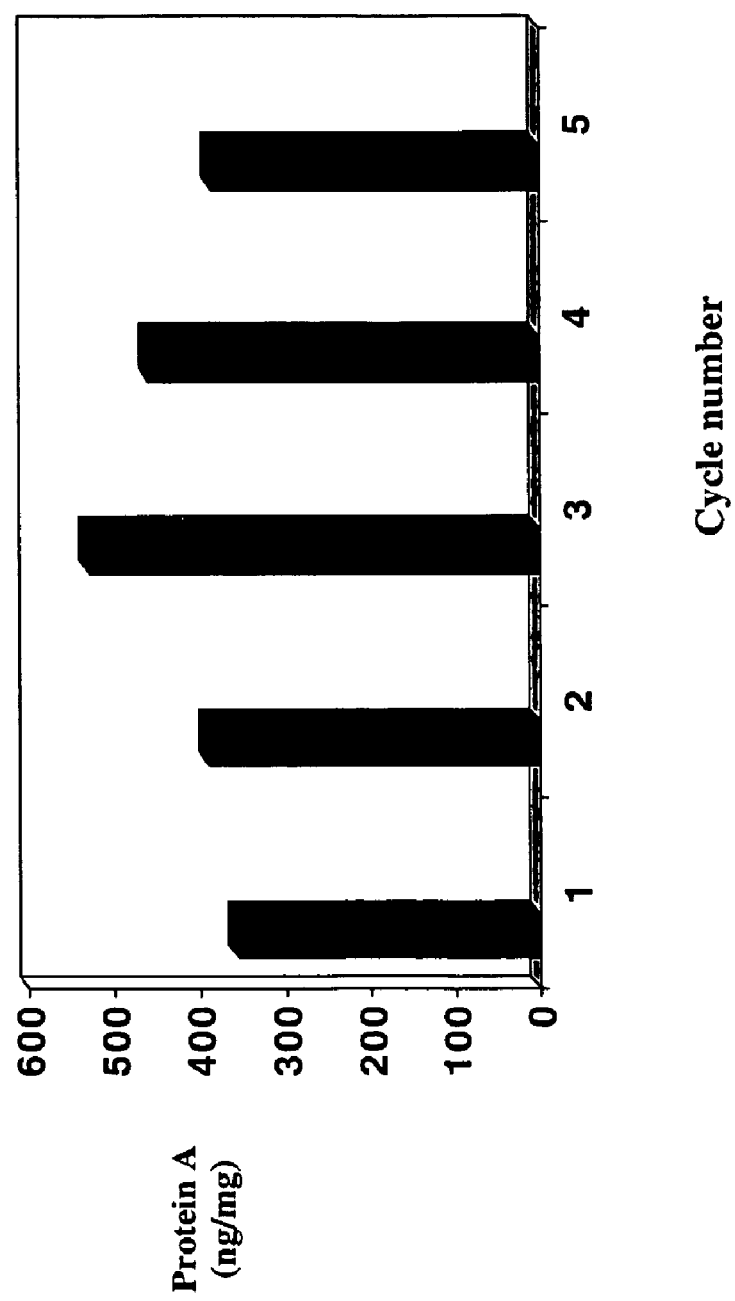
FIG. 2 shows the levels of leaked recombinant protein A in antibody eluates from Streamline™ recombinant protein A chromatography with single-point attached protein A in thioether linkage.

FIG. 2 shows the levels of leaked recombinant protein A in antibody eluates from Streamline™ recombinant protein A chromatography with single-point attached protein A in thioether linkage. The cycle number refers to repeated use after elution with 1 M sodium chloride and re-equilibration. Whereas leakage from cell culture broth from hybridoma cell culture was typically in the order of 500 ppm, other cell types gave levels as high as 1000 ppm. An overview on the rate of leakage from differently sourced matrices is given in Table 1; chromatography was performed according to manufacturer' instruction.

TABLE 1

| Matrix | Supplier | Coupling chemistry | Typical leakage p.p.m | Working Capacity (mgml$^{-1}$) | Flow Rate (cmh$^{-1}$) |
|---|---|---|---|---|---|
| Native Protein A Sepharose 4FF | Amersham-Biosciences | Multi point attached CNBr | 10-20 | 5-20 | 30-300 |
| rmp Protein A Sepharose | Amersham-Biosciences | Multi point attached | 10-20 | 5-20 | 30-300 |
| Poros A High Capacity | Applied Biosystems | Multi point attached | 10-50 | 10 | 500-1000 |
| Protein A Ceramic HyperD | Biosepra | Multi point attached | Up to 300 | 10-20 | 200-500 |
| rProtein A Sepharose | Amersham-Biosciences | Single point attached Thioether linkage | 50-1000 | 20-40 | 30-300 |
| MabSelect | Amersham-Biosciences | Single point attached Thioether linkage | 50-1000 | 20-40 | 500 |
| STREAM-LINE rProtein A | Amersham-Biosciences | Single point attached Thioether linkage | 50-1000 | 20-40 | 200-400 |

Figure 3:
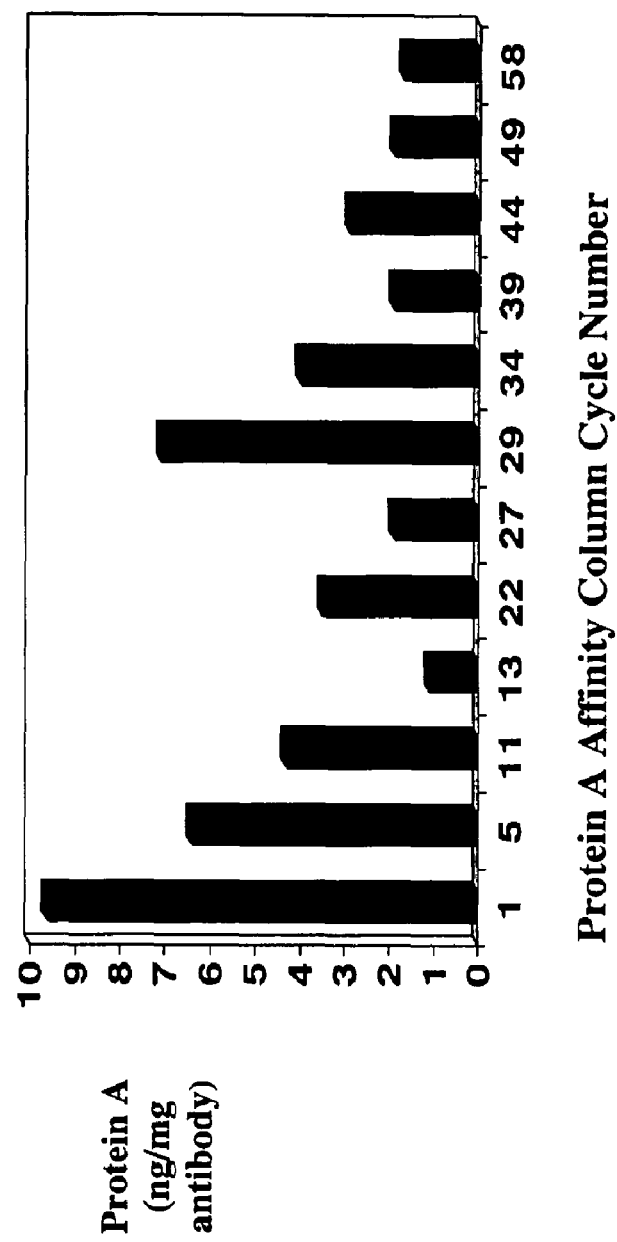
FIG. 3 further provides data on insubstantially reduced leakage of contaminant protein A during repeated runs of the protein A affinity chromatography.

FIG. 3 further provides data on insubstantially reduced leakage of contaminant protein A during repeated runs of the protein A affinity chromatography with the same affinity matrix material; wild-type protein A multipoint-attached Sepharose 4 FF (Amersham-Biosciences) was repeatedly used as described in section 2.1 below and the level of contaminant protein A in the eluate, before any further processing of eluate, was determined by Elisa as described above.

2. Protein A and Sepharose Q Chromatography 2.1 Protein A Affinity Chromatography with Streamline™

Cell culture supernatant from a NSO myeloma cell culture was crudely purifed by centrifugation and in depth filtration and concentrated by ultrafiltration; ultrafiltration was also used to exchange the culture fluid to PBS pH 7.5. The titer of the antibody #5 produced by the cells was 0.2 mg/ml, a total of 1 L buffer-exchanged supernatant was loaded. The pI of the monoclonal antibody #5 was 8.5. The protein A Streamline™ column (5.0 ml volume) was previously equilibrated with 10 column volumes of 50 mM glycine/glycinate pH 8.8, 4.3 M NaCl; flow rate was at 200 cm/h. For loading, the column was operated at a flow rate of 50 cmh$^{-1}$; loading capacity was about 20 mg/ml matrix material). Before elution, the column was washed with at least 10 column volumes of glycine equilibration buffer supplemented with additional 200 mM NaCl and 0.1% Tween-20. Elution was achieved with elution buffer made up of 0.1 M glycine/HCl pH 4.0 buffer. Immediately after elution, fractions of eluate comprising the antibody peak were neutralized with an adequate aliquot of 0.5 M TrisHCl pH 7.5 and buffer exchanged with an Amicon diafiltration device with loading/equilibration buffer (lOMM Tris/HCl pH 8.0, 50 mM NaCl) of the present invention for the subsequent anion exchanger step for preventing longer exposure to acidic pH.

The antibody concentration and the contaminant protein A concentration were determined as described above. The level of contaminant protein A in the eluate amounted to 1434 ng/mg antibody before and amounted to 1650 ng/mg antibody after diafiltration. The recovery of antibody based on the titer of the buffer exchanged supernatant solution prior to loading was 81%; the concentration of antibody in the diafiltrated solution was 3.6 mg/ml.

2.2 Q-Sepharose FF Anion Exchange Step in Non-binding Mode

The purified antibody from section 2.1 was further processed as described: A 5.0 ml Q-Sepharose FF column (Amersham-Biosciences) was packed 10 ml of 0.1 M NaOH, followed by 2 column volumes of 0.1 M Tris pH 8, and equilibrated in 10 column volumes of 10 mM Tris pH 8/50 mM NaCl, at a flow rate of 75 cm/h. After equilibration, the flow rate was reduced to 50 cm/h. 6 ml of the diafiltrated antibody solution was loaded onto the column and the flow-through was collected for further processing; the flow-throught was continued to be collected until, after having loaded the column with the initial 6 ml and having continued thereafter with pure loading or equilibration buffer 10 mM Tris pH 8, 50 mM NaCl, the absorption of the flow-through monitored at 280 nm was back to baseline. The total recovery of antibody in the flow-through was 23 mg antibody (87%). Determination of the level of contaminant protein A resulted in <3 ng/mg antibody. Further processing of this Q-Sepharose purified antibody batch by gel filtration (size exclusion chromatography, SEC) over Sephacryl S-300 in 10 mM Phosphate pH 7.0, 140 mM NaCl buffer at a flow rate of 10 cm/h with a loading ratio of 15 mg antibody per ml gel was found not change this trace contaminant protein A level substantially any more. By experience, SEC may be used to further reduce levels of about 30-100 ng/mg contaminant protein A to about 1-5 ng/mg. Thus SEC has a very low purification factor with regard to trace amounts of protein A, possibly accounting for affinity interactions in between antibody and contminant A. However, due to the unavoidable dilution of sample and slow processing with allows for same decay of the antibody protein, SEC will allow for 70% recovery only of the amount of antibody loaded. This means SEC will unavoidably result in loss of material whilst requiring much time.

The Q-Sepharose column was recycled for further use by separate elution in 2M NaCl and further equilibration as described above.

3. Protein A and Sepharose Q Purification with Subsequent Cation Exchange Step

In a further experiment, the antibody from exp. 2.2. purified in a non-binding mode by Q-Sepharose anion exchange was used. Instead of testing a further, final SEC purification step, the antibody harvested in the flow-through of the Sepharose Q column was subjected to a second cation exchanger step with a SP-Sepharose FF (SP=Sulphopropyl-) matrix from Amersham-Biosciences. The SP-Sepharose FF allowed of a flow rate of 100 cm/h with a reproducible yield of 93% antibody after loading, washing and elution of the antibody from the cation exchanger.

For loading, the pH of the antibody solution obtained after Sepharose Q purification step was adjusted to pH 4.5-5.0 with 50 mM acetate buffer pH 4.5. The loading capacity was set with 10 mg/ml matrix material at a conductivity of load of 17 mS/cm. The 50 mM acetate buffer was further used for washing to baseline. A 50 mM Na acetate pH 4.5, 1 M NaCl high salt buffer was used for elution of antibody; monomeric antibody eluted first, whereas aggregates used to elute in the tail fractions at high ionic strength. Use of a less steep salt gradient by implementation of a salt gradient in the elution buffer before pumping on the column is equally feasible; direct application of a high-salt buffer results in less diluted antibody and consequently more precisely sampling and shorter times of residence in the acidic solution. After elution, the acidic buffer was quickly exchanged for PBS pH 7.5. The level of contaminant protein A in the pooled eluate was determined with <0.4 ng/mg antibody, the antibody was shown to be >99% monomeric by menas of size exclusion HPLC.

4. Streamline™ Protein A Affinity Chromatography with Custom-made, Multipoint-attached Protein A This multipoint-attached Streamline™ protein A-affinity matrix was custom made and supplied by Pharmacia Biotech (now Amersham-Pharmacia). It was made up by the manufacturer by coupling the same 34 kD Streamline™-type recombinant protein A having a terminal Cys residue to the same Sepharose matrix material, but used traditional CNBr chemistry for activation and coupling instead of epoxide-mediated activation and selective reaction conditions for coupling of —SH groups only (see product information from manufacturer). The method of exp. 2.1 was repeated and the level of contaminant protein A was determined with 353 ng/mg antibody. This means that the mode of coupling of the protein A to the matrix material partly accounts for increased protein leakage from high-capacity, single-point attached recombinant protein A affinity matrices; the modifications in amino acid sequence introduced into such recombinant protein A as compared to full-length wild-type protein A contribute considerably to increased protein leakage, too.

5. Parallel Comparison of Methods: Comparison with Miles Method (U.S. Pat. No. 4,983,722)

The Miles Patent (No: 4,983,722) claims that binding DEAE Sepharose used as a second chromatography step with a salt gradient (0.025M to 0.25M NaCl) for elution can reduce the leached Protein A content in the eluate to less than 15 ng/mg antibody (range of protein A was 0.9 to 14 ng/mg of antibody).

TABLE 2

Comparison of Protein A residues in eluate samples of 6A1 Antibody purified on single and multipoint attached Protein A affinity matrices

| Matrix | Sample | Protein A levels (ng/mg) |
|---|---|---|
| rProtein A Sepharose (single point attached) | Protein A eluate | 20.2 |
| rmp Protein A Sepharose (multi-point attached) | Protein A eluate | 2.16 |
| Native Protein A Sepharose (multipoint attached) | Protein A eluate | <2.0 |

The aim of these experiments was to confirm these results using MabSelect (new single point attached rProtein A matrix) with a lower pI antibody (pI 6.5-7.5), and to directly compare the non-binding Q-Sepharose method (using different equilibration/loading buffers) with the Miles Patent method.

Method Applied:

The purification of 6A1 antibody (pI 6.5-7.5) included two chromatography steps consisting of MabSelect Protein A step followed by Q-Sepharose anion exchange chromatography (non-binding), or DEAE Sepharose chromatography (binding) step. See L0 9007 and L0 9375

| MabSelect Protein A Chromatography: | |
|---|---|
| Column matrix | Mab Select recombinant Protein A (single point attached rPA) |
| Column dimensions | 1.6 cm internal diameter × 15 cm bed height |
| Column volume | 30 mL |
| Operational flow rate | 500 cm/hr (16.80 mL/min) |
| Clean | 6M guanidine HCL (2 column volumes) |
| Loading capacity | 35 mg/ml matrix |
| Equilibration | 50 mM glycine/glycinate pH 8.0/250 mM NaCL (8 column volumes) |
| Post load wash | 50 mM glycine/glycinate pH 8.0/250 mM NaCL (8 column volumes) |
| Elution buffer | 100 mM glycine pH 3.50 (6 column volumes) |
| Wash | 100 mM Citric acid pH 2.1 (2 column volumes) |

The culture supernatant containing 6A1 antibody was purified on a MabSelect column (30 ml), connected to an AKTA FPLC system. The conditions used were as described in the table above. The antibody was eluted using 0.1M glycine pH 3.5. Following elution the eluate pH was adjusted to pH 7.0, and then the eluate sample was divided into 5 aliquots; each aliquot was then diafiltered into a different buffer for anion exchange chromatography.

The first aliquot was diafiltered into 50 mMTrisHCl pH8/75mMNaCl for Q-Sepharose chromatography run 1. The second aliquot was diafiltered into 50 mMTrisHCl pH8/100 mMNaCl for Q-Sepharose chromatography Run 2. The third aliquot was diafiltered into 20 mM sodium phosphate pH6.5/80 mM NaCl for Q-Sepharose chromatography Run 3. Aliquots four and five were buffer exchanged into 25 mMTris HCl pH 8.0/25 mMNaCl for evaluation of binding DEAE Sepharose method described in Miles patent. The difference between Runs 4 & 5 is that in Run 4 the main peak was collected as one fraction and diafiltered into standard phosphate buffered saline prior to analysis whereas in Run 5, the elution peak was fractionated and dialysed into a phosphate buffer prepared as described in the Miles Patent.

The conditions for each of the five column runs are described below:

| Q-Sepharose Chromatography: Run 1 | |
|---|---|
| Column matrix | Q-Sepharose Fast Flow |
| Column dimensions | 1.6 cm internal diameter × 8 cm bed height |
| Column volume | 16 mL |
| Column preparation | Packed in 0.1M Sodium Hydroxide at 150 cm/hr |
| Operational flow rate | 100 cm/hr (3.35 mL/min) |
| Clean | 0.1M Sodium Hydroxide (2 column volumes) |
| Loading capacity | 15 mg/ml matrix |
| Equilibration | 50 mM TrisHCl pH 8.0/75 mM NaCl (8 column volumes) |
| Post load wash | 50 mM TrisHCl pH 8.0/75 mM NaCl (5 column volumes) |
| Strip buffer | 2M Sodium Chloride (2 column volumes) |
| Wash | 0.1M Sodium Hydroxide (2 column volumes) |

| Q-Sepharose Chromatography: Run 2 | |
|---|---|
| Column matrix | Q-Sepharose Fast Flow |
| Column dimensions | 1.6 cm internal diameter × 8 cm bed height |
| Column volume | 16 mL |
| Column preparation | Packed in 0.1M Sodium Hydroxide at 150 cm/hr |
| Operational flow rate | 100 cm/hr (3.35 mL/min) |
| Clean | 0.1M Sodium Hydroxide (2 column volumes) |
| Loading capacity | 7.5 mg/ml matrix |
| Equilibration | 50 mM TrisHCl pH 8.0/100 mM NaCl (8 column volumes) |
| Post load wash | 50 mM TrisHCl pH 8.0/100 mM NaCl (5 column volumes) |
| Strip buffer | 2M Sodium Chloride (2 column volumes) |
| Wash | 0.1M Sodium Hydroxide (2 column volumes) |

| Q-Sepharose Chromatography: Run 3 | |
|---|---|
| Column matrix | Q-Sepharose Fast Flow |
| Column dimensions | 1.6 cm internal diameter × 8 cm bed height |
| Column volume | 16 mL |
| Column preparation | Packed in 0.1M Sodium Hydroxide at 150 cm/hr |
| Operational flow rate | 100 cm/hr (3.35 mL/min) |
| Clean | 0.1M Sodium Hydroxide (2 column volumes) |
| Loading capacity | 7.5 mg/ml matrix |
| Equilibration | 20 mM Sodium phosphate pH 6.5/80 mM NaCl |
| Post load wash | 20 mM Sodium phosphate pH 6.5/80 mM NaCl (5 column volumes) |
| Strip buffer | 2M Sodium Chloride (2 column volumes) |
| Wash | 0.1M Sodium Hydroxide (2 column volumes) |

| DEAE Sepharose: Run 4 | |
|---|---|
| Column matrix | DEAE Sepharose |
| Column dimensions | 1.6 cm internal diameter × 8 cm bed height |
| Column volume | 16 mL |
| Column preparation | Packed in equilibration buffer at 150 cm/hr |
| Operational flow rate | 100 cm/hr (3.35 mL/min) |
| Clean | 0.1M Sodium Hydroxide (2 column volumes) |
| Loading capacity | 7.5 mg/ml matrix |
| Equilibration | 25 mM TrisHCl pH 8.6/25 mM NaCl (8 column volumes) |
| Post load wash | 25 mM TrisHCl pH 8.6/25 mM NaCl (5 column volumes) |
| Elution buffer | 25 mM TrisHCl pH 8.6/25 mM NaCl To 25 mM TrisHCl pH 8.6/250 mM NaCl (10 column volumes) |
| Wash | 2M Sodium Chloride (2 column volumes) |

| DEAE Sepharose binding method: Run 5 (Miles method) | |
|---|---|
| Column matrix | DEAE Sepharose |
| Column dimensions | 1.6 cm internal diameter × 8 cm bed height |
| Column volume | 16 mL |
| Column preparation | Packed in equilibration buffer at 150 cm/hr |
| Operational flow rate | 100 cm/hr (3.35 mL/min) |
| Clean | 0.1M Sodium Hydroxide (2 column volumes) |
| Loading capacity | 7.5 mg/ml matrix |
| Equilibration | 25 mM TrisHCl pH 8.6/25 mM NaCl (8 column volumes) |
| Post load wash | 25 mM TrisHCl pH 8.6/25 mM NaCl (5 column volumes) |
| Elution buffer | 25 mM TrisHCl pH 8.6/25 mM NaCl To 25 mM TrisHCl pH 8.6/250 mM NaCl (10 column volumes) |
| Wash | 2M Sodium Chloride (2 column volumes) |

The properties of the different buffers used in this study are shown in Table 3.

Eluate samples generated from the 5 ion exchange runs were assayed for Protein A levels in the rPA ELISA. The results are shown in Table 4.

TABLE 3

Buffers used in this study

| Equilibration Buffer | Run Number | Conductivity (ms/cm) | Resin | pH |
|---|---|---|---|---|
| 50 mM TrisHCl pH 8.0/75 mM NaCl | 1 | 10.74 | Q-Sepharose (non-binding) | 8.00 |
| 50 mM TrisHCl pH 8.0/100 mM NaCl | 2 | 12.85 | Q-Sepharose (non-binding) | 8.01 |
| 20 mM Sodium phosphate pH 6.5/80 mM NaCl | 3 | 10.20 | Q-Sepharose (non-binding) | 6.50 |
| 25 mM TrisHCl pH 8.6/25 mM NaCl | 4/5 | 3.35 | DEAE-Sepharose (binding) | 8.60 |
| 25 mM TrisHCl pH 8.6/250 mM NaCl* | 4/5 | 24.54 | DEAE-Sepharose (binding) | 8.61 |

*Gradient elution buffer

Fractions across the elution profile of DEAE-Sepharose Run 5 (Miles method) were collected and analysed in the rProtein A ELISA; the results are shown in Table 5.

TABLE 4 rProtein A ELISA Results:

| Sample ID | rProtein A levels (ng/mg) | Antibody concentration (mg/ml) | % Recovery | Elution Volumes (CV's)* |
|---|---|---|---|---|
| Q-Sepharose eluate Run 1 | <0.4 | 1.42 | 82 | 4.5 |
| Q-Sepharose eluate Run 2 | 2.94 | 1.49 | 70 | 3.5 |
| Q-Sepharose eluate Run 3 | 0.73 | 1.86 | 85 | 3.4 |
| DEAE Sepharose eluate pool Run 4 (pool of all fractions) | 1.72 | 2.16 | 75 | 2.5 |
| DEAE Sepharose eluate pool (Miles Method) Run 5 (pool of fractions 2 to 6) | 1.55 | 1.83 | 73 | 3 |

*Where CV's denotes column volumes

TABLE 5

Levels of rProtein A in Eluate fractions across the elution peak obtained during binding DEAE-Sepharose separation (Miles Method); Run 5.

| Fraction Number | rProtein A levels (ng/mg) | Absorbance ($A_{280}$) |
|---|---|---|
| 1 | 3.33 | 0.018 |
| 2 | 0.4 | 0.108 |
| 3 | 0.4 | 0.22 |
| 4 | 0.4 | 0.169 |
| 5 | 2.01 | 0.092 |
| 6 | 16.7 | 0.042 |
| 7 | 6.38 | 0.016 |

The highest recovery (85%) and best clearance of rProtein A for this antibody (6A1; pI 6.5-7.5) was obtained under non-binding conditions on Q-Sepharose using 20 mM sodium phosphate pH 6.5/80 mM NaCl buffer (corresponding to Run 3). Run 1 also showed good recovery (82%) and rProtein A clearance however, the elution volume for this run was significantly higher than expected for a non-binding method; suggesting partial retardation of the antibody on the column in this buffer system. Increasing the NaCl concentration (Run 2) resulted in lower rProtein A clearance, hence the buffer system used in Run 3 was more appropriate for this antibody. It has been our previous observation that the buffer system used in Run 1 is more appropriate for high pI antibodies and that used in Run 3 is particularly useful for neutral or slightly acidic antibodies. These experiments were done at similar capacities (7.5 mg/ml resin) we would expect to be able to use this non-binding method at much higher capacities (>30 mg/ml). We would expect this non-binding method to be applicable to many anion exchangers for example Q-Hyper D in addition to anion exchange membrane adsorbers (such as Mustang Q, Intercept Q and Sartobind Q). We would also expect this process to be more applicable to large scale production compared to the Miles method as higher capacities etc can be applied.

In the case of Run 5 (Miles method), fractionation of rProtein A was observed across the main elution peak as shown in table 5. Careful pooling of fractions is therefore required to ensure good clearance of rProtein A. This had an impact on recovery (73%) and even in this case did not give as good clearance as obtained with the non-binding method. For the Miles method therefore it is more difficult to achieve good clearance and high recovery for cell lines/antibodies in cases where very high leakage is observed (such as that commonly obtained with single point attached matrices)

The data from Run 5 is representative of the results obtained by and the conditions described in the Miles patent.

An overview of method comparisons and the data obtained is shown in Table 6, below.

TABLE 6

Summary of rProtein A Levels at Different Stages of Antibody Purification.

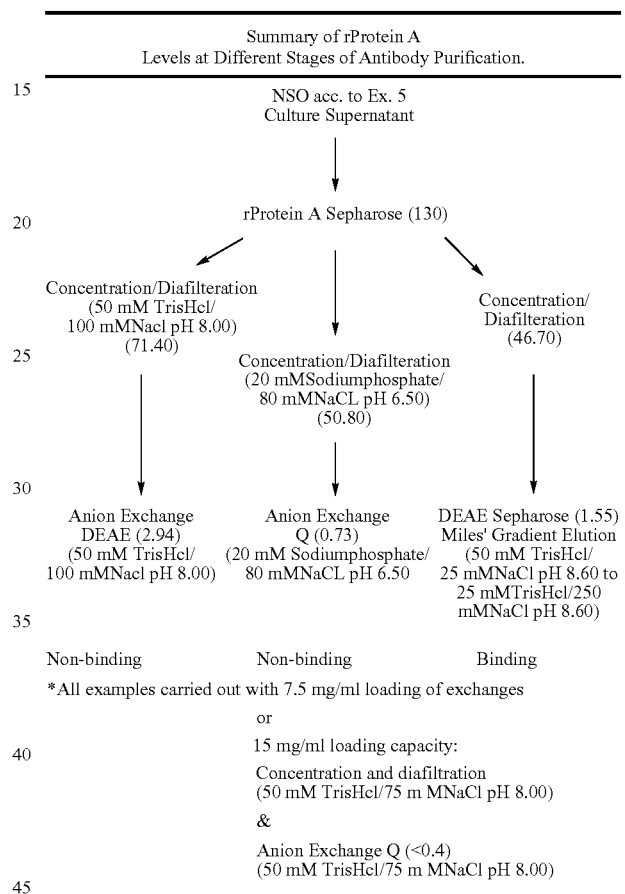

*All examples carried out with 7.5 mg/ml loading of exchanges or 15 mg/ml loading capacity:

Concentration and diafiltration
(50 mM TrisHcl/75 m MNaCl pH 8.00)

&

Anion Exchange Q (<0.4)
(50 mM TrisHcl/75 m MNaCl pH 8.00)

Note
Levels of rProtein A are shown in brackets ng/mg; note that not all NSO clonal cell lines supernatants give similar contamination levels of protein A.

6. Purification of a High pI Antibody

A high pI antibody (pI 9.0-9.3) was purified using Protein A Affinity Chromatography (MabSelect—single point attached recombinant Protein A matrix), followed by Q-Sepharose anion exchange chromatography (under non binding conditions; for removal of trace contaminants) followed by SP-Sepharose cation exchange chromatography (under binding conditions for removal of aggregates).

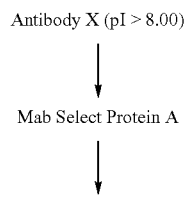

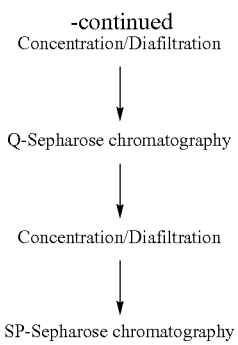

Experimental Materials and Methods

| MabSelect Protein A Chromatography: | |
|---|---|
| Column matrix | Mab Select recombinant Protein A (single point attached rPA) |
| Column dimensions | 1.6 cm internal diameter × 15 cm bed height |
| Column volume | 30 mL |
| Operational flow rate | 500 cm/hr (16.80 mL/min) |
| Clean | 6M guanidine HCL (2 column volumes) |
| Loading capacity | 35 mg/ml matrix |
| Equilibration | 50 mM glycine/glycinate pH 8.0/250 mM NaCL (8 column volumes) |
| Post load wash | 50 mM glycine/glycinate pH 8.0/250 mM NaCL (8 column volumes) |
| Elution buffer | 100 mM glycine pH 3.50 (6 column volumes) |
| Wash | 100 mM Citric acid pH 2.1 (2 column volumes) |

Culture supernatant containing high pI antibody was purified on a MabSelect Protein A Affinity column (30 ml), connected to an AKTA FPLC system. The conditions used were as described in the table above. The antibody was eluted using 0.1M glycine pH 3.5. Following elution, the eluate was held at pH 3.69 (no adjustment required) for 60 min (low pH virus inactivation step), and then neutralised to pH 8 using 2 M Tris Base. Three cycles on Protein A were performed; product recovery was determined by A280nm and is shown in Table 7 for each cycle.

TABLE 7

| % Recovery on Mab Select Protein A Column | |
|---|---|
| Cycle Number | % Recovery |
| 1 | 81 |
| 2 | 81 |
| 3 | 80 |

After MabSelect Protein A chromatography the eluates from each of the three cycles were pooled together and buffer exchanged into 25 mM Tris pH 8.0 (Q-Sepharose equilibration buffer) using an Amicon stirred cell concentrator fitted with 10 kDa Millipore membrane.

| Q-Sepharose Chromatography: | |
|---|---|
| Column matrix | Q-Sepharose Fast Flow |
| Column dimensions | 1.6 cm internal diameter × 15 cm bed height |
| Column volume | 30 mL |
| Column preparation | Packed in 0.1M Sodium Hydroxide at 225 cm/hr |
| Operational flow rate | 150 cm/hr (5.0 mL/min) |
| Clean | 0.1M Sodium Hydroxide (2 column volumes) |
| Loading capacity | 40 mg/ml matrix |
| Equilibration | 20 mM Tris pH 8.0 (8 column volumes) |
| Post load wash | 20 mM Tris pH 8.0 (5 column volumes) |
| Strip buffer | 20 mM Tris pH 8.0/2M NaCl (2 column volumes) |
| Wash | 0.1M Sodium Hydroxide (2 column volumes) |

40ml of concentrated/diafiltered MabSelect Protein A eluate was loaded on Q-Sepharose column at a loading capacity of 40mg/ml matrix. The column was operated in a non-binding mode and the unbound fraction containing the antibody was collected. The recovery on this step was 69% by A280. This is slightly lower than obtained under these conditions for this antibody and may be due inaccurate estimation of the load volume due to hold up volume in the FPLC sample pump.

Following Q-Sepharose chromatography, the unbound fraction was concentrated to 13.98 mg/ml and diafiltered into SP-Sepharose equilibration buffer (25 mM Sodium acetate pH5.0/25 mM NaCl) using an Amicon stirred cell fitted with 10 kDa Millipore Ultrafilteration membrane.

| SP-Sepharose Chromatography: | |
|---|---|
| Column matrix | Q-Sepharose Fast Flow |
| Column dimensions | 1.6 cm internal diameter × 15 cm bed height |
| Column volume | 30 mL |
| Column preparation | Packed in 0.1M Sodium Hydroxide at 150 cm/hr |
| Operational flow rate | 100 cm/hr (3.35 mL/min) |
| Clean | 0.1M Sodium Hydroxide (2 column volumes) |
| Loading capacity | 10 mg/ml matrix |
| Equilibration | 25 mM Sodium acetate pH 5.00/25 mM NaCl (8 column volumes) |
| Post load wash | 25 mM Sodium acetate pH 5.00/25 mM NaCl (6 column volumes) |
| Elution | 25 mM Sodium acetate pH 5.00/186 mM NaCl (25 column volumes) |
| Strip buffer | 25 mM Sodium acetate pH 5.00/2M NaCl (2 column volumes) |
| Wash | 0.1M Sodium Hydroxide (2 column volumes) |

24ml of buffer exchanged Q-Sepharose eluate was loaded onto the SP-Sepharose column at a loading capacity of 10 mg/ml matrix. The column was operated in a binding mode; the eluate was collected as fractions. Fractions across the elution profile were analysed by GP-HPLC to determine aggregate levels results and are shown in Table 8. Samples following each chromatography step were collected and analysed for rProtein A residues, results are presented in Table 9.

TABLE 8

| rProtein A ELISA Results after each chromatography step | | |
|---|---|---|
| Sample ID | rProtein A levels(ng/mg) | Antibody concentration (mg/ml) |
| MabSelect Protein A eluate (after conc/diaf) | 2.64 | 46.7 |
| Q-Sepharose eluate | <4 | 8.10 |
| SP-Sepharose eluate pool F(1-16) | <4 | 1.79 |

TABLE 9

GP-HPLC Analysis of SP-Sepharose fractions

| Sample ID | % Aggregates | Absorbance ($A_{280}$) |
|---|---|---|
| SP eluate pool F(1-3) | 0.57 | 11.2 |
| SP eluate pool F(4-6) | 1.10 | 2.7 |
| SP eluate pool F(7-9) | 2.07 | 0.655 |
| SP eluate pool F(10-12) | 2.12 | 0.351 |
| SP eluate pool F(13-15) | 2.56 | 0.208 |

Figure 4:
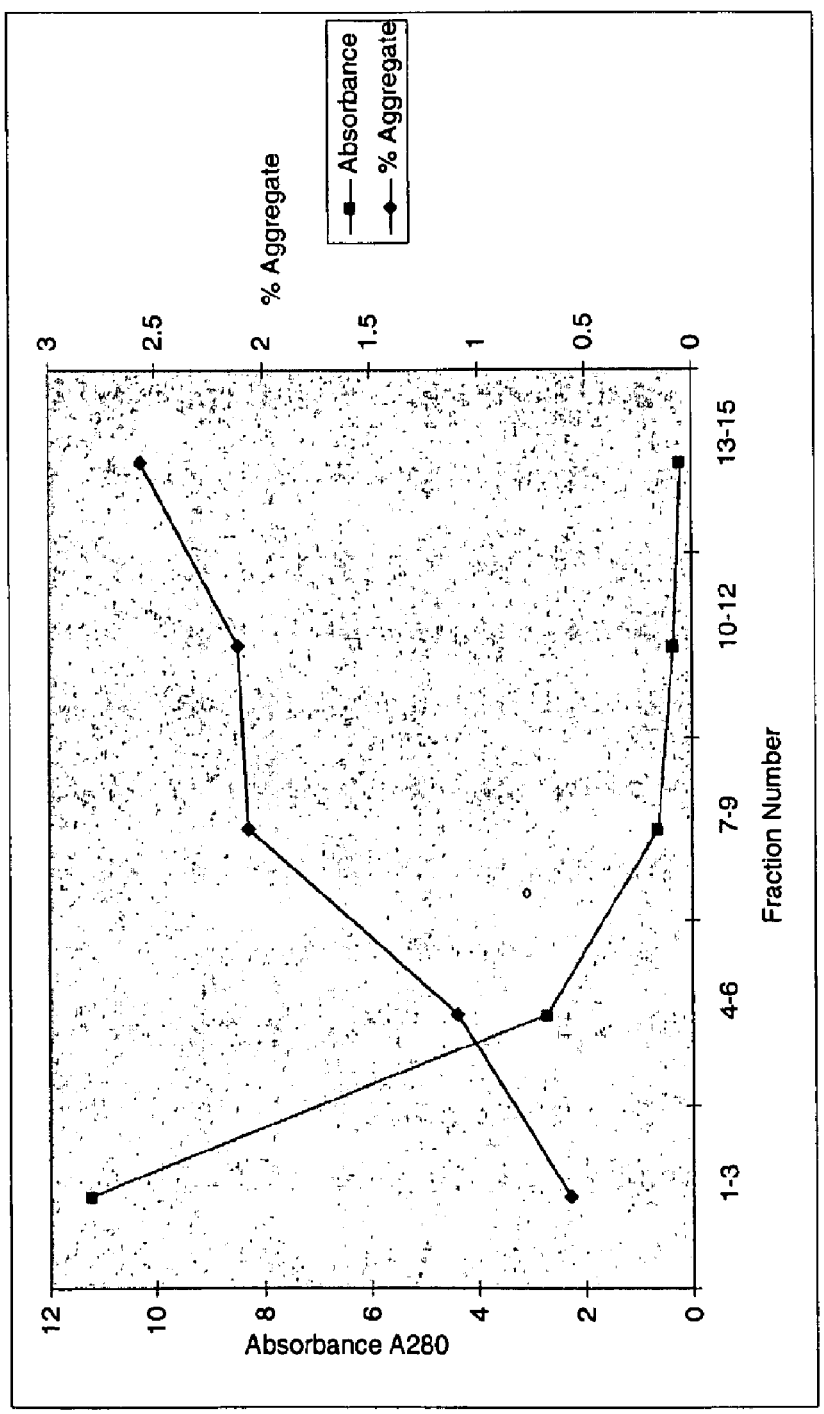
FIG. 4 shows results of fractionation of aggregates during step elution of the antibody peak, as described further herein.

Conclusion: Fractionation of aggregates was observed during step elution of the antibody peak; see FIG. 4, with the aggregate-enriched fractions eluting later (on the tail end of the elution peak) compared to non-aggregate containing fractions. The tail fractions can be omitted from the main pool to obtain 99% monomeric pool and still have high recovery (>95%).

7. Purification Using Ceramic 0-HyperD® F als a First Anion Exchanger

Figure 5:
FIG. 5 shows outline of separation schemes, as further described herein.
Figure 5:

Q-HyperD® F (Biosepra-Brand of chromatographic supports) was purchased from Ciphergen Biosystems Ltd., Guildford, UK. The processing of a pI 8-9 antibody expressed from NS0 cells by Mab-Select Protein A affinity chromatography was conducted essentially as described in example 5. Further essentially as described in example 5 (for Runs 1-3), Q anion exchange chromatography in flow-through mode was then applied to the Protein A-affinity column eluate except that Q-Sepharose, except for a comparative run, was replaced by Q-Hyper DF (Biosepra®) under varying conditions of buffer salt, buffer pH and conductivity. The respective conditions are outlined in the scheme according to FIG. 5; applying a very low conductivity of less than 2 mS/cm, namely at about 1.26 mS/cm, proved superior with regard to deriching contaminating protein A to the utmost extend possible and achieving results equal to those obtainable with Sepharose Q material. However, for large scale industrial manufacture, the ceramic HyperD material offers advantages in view of life time, robustness and compressibility (processing time, flow rate). Hence conductivity is a very important parameter to be testeed and optimized for different column materials.

We claim:

1. Method of purifying an antibody comprising the steps of:
   firstly, purifying an antibody by means of protein A affinity chromatography wherein the protein A is a native protein A or a functional derivative thereof,
   secondly, loading the purified antibody comprising a protein A-contaminant, wherein said protein A-contaminant is obtained upon eluting bound antibody from said protein A affinity chromatography, on a first ion exchanger under conditions which allow for binding of the protein A or its derivative,
   thirdly, collecting the antibody loaded onto the first ion exchanger in the flow-through of the first ion exchanger whilst a contaminant protein A is bound to the first ion exchanger, wherein the first ion exchanger is an anion exchanger,
   further purifying the antibody by loading on, binding to and eluting it from a second ion exchanger, and
   discarding a tail fraction of the eluate of the second ion exchanger such that a monomeric antibody fraction is enriched as a purified antibody pool.

2. Method according to claim 1, characterized in that the protein A of the protein A affinity chromatography is a recombinant protein A that is engineered such as to allow of single-point attachment to the material.

3. Method according to claim 2, characterized in that the recombinant protein A is attached by at least 50% via a thioether bond from a cysteine to the material of the protein A affinity chromatography.

4. Method according to claim 1, characterized in that at least 70% of the amount of antibody loaded onto the first ion exchanger is recovered in the flow-through.

5. Method according to claim 4, characterized in that the antibody has a pI of at least 7.5.

6. Method according to claim 4, characterized in that the second ion exchanger is a cation exchanger.

7. Method according to claim 1 wherein said anion exchanger is a ceramic matrix.

8. Method according to claim 7 wherein said ceramic matrix comprises quaternary ammonium functional groups.

9. Method according to claim 1, characterized in that the antibody has a pI of at least 6.5.

10. Method according to claim 1, characterized in that the antibody is a monoclonal antibody.

11. Method according to claim 10, characterized in that the antibody is harvested from a cell culture prior to purifying the antibody by means of protein A affinity chromatography.

12. Method according to claim 11, characterized in that the antibody is harvested from a mammalian cell culture.

13. Method according to claim 12, characterized in that the antibody that is to be purified by means of protein A affinity chromatography is not treated so as to inactivate proteases.

14. Method according to claim 11, characterized in that the antibody that is to be purified by means of protein A affinity chromatography is not treated so as to inactivate proteases.

15. Method according to claim 14 wherein said anion exchanger is a ceramic matrix.

16. Method according to claim 15 wherein said ceramic matrix comprises quaternary ammonium functional groups.

17. Method according to claim 10, characterized in that the antibody is harvested from a cell culture prior to purifying the antibody by means of protein A affinity chromatography.

18. Method according to claim 17, characterized in that the antibody is harvested from a mammalian cell culture.

19. Method according to claim 18, characterized in that the antibody that is to be purified by means of protein A affinity chromatography is not treated with a chemical additive so as to inactivate proteases.

20. Method according to claim 17, characterized in that the antibody that is to be purified by means of protein A affinity chromatography is not treated so as to inactivate proteases.

21. Method according to claim 10, characterized in that the antibody is an IgG antibody.

22. Method according to claim 21, characterized in that the IgG antibody is in its Fc portion that is relevant for binding to protein A, of such species origin and IgG subclass origin which origins allow for high affinity binding to protein A.

23. Method according to claim 22, characterized in that the IgG antibody is a human IgG1, IgG2 or IgG4 with regard to the Fc portion of the antibody.

24. Method according to claim 21 wherein the IgG antibody is a chimeric or CDR-grafted IgG antibody.

* * * * *